(12) United States Patent
Elharis

(10) Patent No.: US 11,441,466 B2
(45) Date of Patent: Sep. 13, 2022

(54) SYSTEMS AND METHODS FOR DETERMINING EXHAUST FLOW RATE

(71) Applicant: CUMMINS EMISSION SOLUTIONS INC., Columbus, IN (US)

(72) Inventor: Tarek Elharis, Greenwood, IN (US)

(73) Assignee: Cummins Emission Solutions Inc., Columbus, IN (US)

(*) Notice: Subject to any disclaimer, the term of this patent is extended or adjusted under 35 U.S.C. 154(b) by 22 days.

(21) Appl. No.: 16/968,952

(22) PCT Filed: Feb. 15, 2018

(86) PCT No.: PCT/US2018/018368
§ 371 (c)(1),
(2) Date: Aug. 11, 2020

(87) PCT Pub. No.: WO2019/160551
PCT Pub. Date: Aug. 22, 2019

(65) Prior Publication Data
US 2020/0370456 A1    Nov. 26, 2020

(51) Int. Cl.
*F01N 3/20* (2006.01)
*F01N 3/28* (2006.01)
*G01F 9/00* (2006.01)
*G01N 33/00* (2006.01)

(52) U.S. Cl.
CPC .......... *F01N 3/208* (2013.01); *F01N 3/2803* (2013.01); *G01F 9/00* (2013.01); *G01N 33/0037* (2013.01); *F01N 2900/08* (2013.01); *F01N 2900/1402* (2013.01); *F01N 2900/1411* (2013.01)

(58) Field of Classification Search
CPC combination set(s) only.
See application file for complete search history.

(56) References Cited

U.S. PATENT DOCUMENTS 10,995,647 B2\* 5/2021 Kidd ..................... F01N 11/00
2006/0288801 A1  12/2006 Graze, Jr.
2010/0275581 A1  11/2010 Wada et al.
(Continued)

FOREIGN PATENT DOCUMENTS

CN         103133165       6/2013

OTHER PUBLICATIONS

International Search Report and Written Opinion issued in PCT/US2018/018368, dated Apr. 26, 2018, 16 pages.
(Continued)

*Primary Examiner* — Binh Q Tran
(74) *Attorney, Agent, or Firm* — Foley & Lardner LLP

(57) ABSTRACT

A system for determining an exhaust flow rate of an exhaust gas produced by an engine comprises a first sensor configured to measure an amount of NOx gases in the exhaust gas. A controller is communicatively coupled to the first sensor. The controller is configured to receive a first sensor signal from the first sensor. The controller is also configured to receive a fuel rate signal corresponding to a rate of fuel consumption by the engine. The controller is configured to determine an air-fuel ratio from the first sensor signal and determine a fuel rate from the fuel rate signal. Furthermore, the controller is configured to determine the exhaust flow rate from the air-fuel ratio and the fuel rate.

21 Claims, 6 Drawing Sheets

(56) References Cited

U.S. PATENT DOCUMENTS

| | | |
|---|---|---|
| 2011/0219746 A1* | 9/2011 | Yezerets ............. F02D 41/1454 |
| | | 60/274 |
| 2012/0303245 A1 | 11/2012 | Wang et al. |
| 2013/0064717 A1 | 3/2013 | Masaki et al. |
| 2013/0311065 A1 | 11/2013 | Sun et al. |
| 2016/0258334 A1* | 9/2016 | Aoki ..................... F01N 11/007 |
| 2016/0319725 A1 | 11/2016 | Chandra-Ramadugu et al. |
| 2016/0356196 A1* | 12/2016 | Nakano ................... F01N 3/208 |
| 2017/0030244 A1* | 2/2017 | Hagiwara ............. F01N 13/008 |
| 2017/0044953 A1* | 2/2017 | Shinoda ................. F01N 3/105 |
| 2017/0241321 A1* | 8/2017 | Yoo ......................... F01N 11/00 |
| 2018/0094558 A1* | 4/2018 | Hagimoto ............... F01N 3/208 |

OTHER PUBLICATIONS

Examination Report issued for UK Patent Application No. GB 2012431.9 dated Feb. 8, 2022, 2 pages.

* cited by examiner

SYSTEMS AND METHODS FOR DETERMINING EXHAUST FLOW RATE

CROSS-REFERENCE TO RELATED APPLICATIONS

The present application is a National Phase Application of PCT/US2018/018368, filed Feb. 15, 2018, the contents of which are hereby incorporated by reference in their entirety.

TECHNICAL FIELD

The present disclosure relates generally to aftertreatment systems for use with internal combustion (IC) engines.

BACKGROUND

Exhaust aftertreatment systems are used to receive and treat exhaust gas generated by IC engines. Generally exhaust gas aftertreatment systems comprise any of several different components to reduce the levels of harmful exhaust emissions present in exhaust gas. For example, certain exhaust gas aftertreatment systems for diesel-powered IC engines comprise a selective catalytic reduction (SCR) system, including a catalyst formulated to convert NOx (NO and $NO_2$ in some fraction) into harmless nitrogen gas ($N_2$) and water vapor ($H_2O$) in the presence of ammonia ($NH_3$). Generally in such aftertreatment systems, an exhaust reductant (e.g., a diesel exhaust fluid such as urea) is injected into the SCR system to provide a source of ammonia and mixed with the exhaust gas to partially reduce the NOx gases. The reduction byproducts of the exhaust gas are then fluidically communicated to the catalyst included in the SCR system to decompose substantially all of the NOx gases into relatively harmless byproducts that are expelled out of the aftertreatment system.

Exhaust flow rate of the exhaust gas is an important parameter which may be used for determining engine efficiency, SCR design or operating parameters of the SCR system, for example the amount or frequency of reductant to be inserted into the exhaust gas. Exhaust flow rate may be estimated using various methods such as, for example the engine speed density model. However, this and other methods are not suitable for estimating exhaust flow rate in large engines, for example high horse power (HHP) engines (e.g., having a volumetric capacity in a range of 19 L to 65 L) such as those used for marine application due to complex tuning or otherwise adjustments needed to get relative accuracy. Another method includes determining exhaust flow rate using speed/torque pre-tuned table. However, this methods fails to account for changes in altitudes, engine to engine variation and flow restrictions in the aftertreatment system, for example due to plugging of a filter or a catalyst included in the aftertreatment system.

SUMMARY

Embodiments described herein relate generally to systems and methods for determining an exhaust flow rate of an exhaust gas produced by an engine and, in particular, to systems and methods for determining an air-fuel ratio ("AFR") from an oxygen fraction in the exhaust gas measured by a NOx sensor, and determining the exhaust flow rate from the air-fuel ratio and a fuel rate of the engine.

In a first set of embodiments, a system for determining exhaust flow rate of an exhaust gas produced by an engine comprises a first sensor configured to measure an amount of NOx gases in the exhaust gas. A controller is communicatively coupled to the first sensor. The controller is configured to receive a first sensor signal from the first sensor. The controller is also configured to receive a fuel rate signal corresponding to a rate of fuel consumption by the engine. The controller is configured to determine an air-fuel ratio from the first sensor signal. The controller is also configured to determine a fuel rate from the fuel rate signal. The controller is configured to determine the exhaust flow rate from the air-fuel ratio and the fuel rate.

In another set of embodiments, an aftertreatment system for treating an exhaust gas produced by an engine comprises a selective catalytic reduction system. A first sensor is configured to measure an amount of NOx gases in the exhaust gas flowing into the selective catalytic reduction system. A controller is communicatively coupled to the first sensor. The controller is configured to receive a first sensor signal from the first sensor. The controller is also configured to receive a fuel rate signal corresponding to a rate of fuel consumption by the engine. The controller is configured to determine an air-fuel ratio from the first sensor signal. The controller is also configured to determine a fuel rate from the fuel rate signal. Furthermore, the controller is configured to determine an exhaust flow rate from the air-fuel ratio and the fuel rate.

In yet another set of embodiments, a method of determining an exhaust flow rate of an exhaust gas produced by an engine comprises determining an air-fuel ratio of the exhaust gas. A fuel rate corresponding to a rate of consumption of a fuel by the engine is determined. The exhaust flow rate is determined from the air-fuel ratio and the fuel rate. An exhaust flow rate signal is generated which is indicative of the exhaust flow rate. An amount of reductant inserted into the exhaust gas is adjusted based on the determined exhaust flow rate.

In still another set of embodiments, a control circuitry for determining an exhaust flow rate of an exhaust gas produced by an engine comprises a controller configured to be communicatively coupled to a first sensor for measuring an amount of NOx gases in the exhaust gas. The controller is configured to receive a first sensor signal from the first sensor. The controller is also configured to receive a fuel rate signal corresponding to a rate of fuel consumption by the engine. The controller is configured to determine an air-fuel ratio from the first sensor signal. The controller is also configured to determine a fuel rate from the fuel rate signal. Furthermore, the controller is configured to determine the exhaust flow rate from the air-fuel ratio and the fuel rate, and generate an exhaust flow rate signal indicative of the exhaust flow rate.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF THE DRAWINGS

The foregoing and other features of the present disclosure will become more fully apparent from the following description and appended claims taken in conjunction with the accompanying drawings. Understanding that these drawings depict only several implementations in accordance with the disclosure and are therefore not to be considered limiting of its scope, the disclosure will be described with additional specificity and detail through use of the accompanying drawings.

Figure 1:
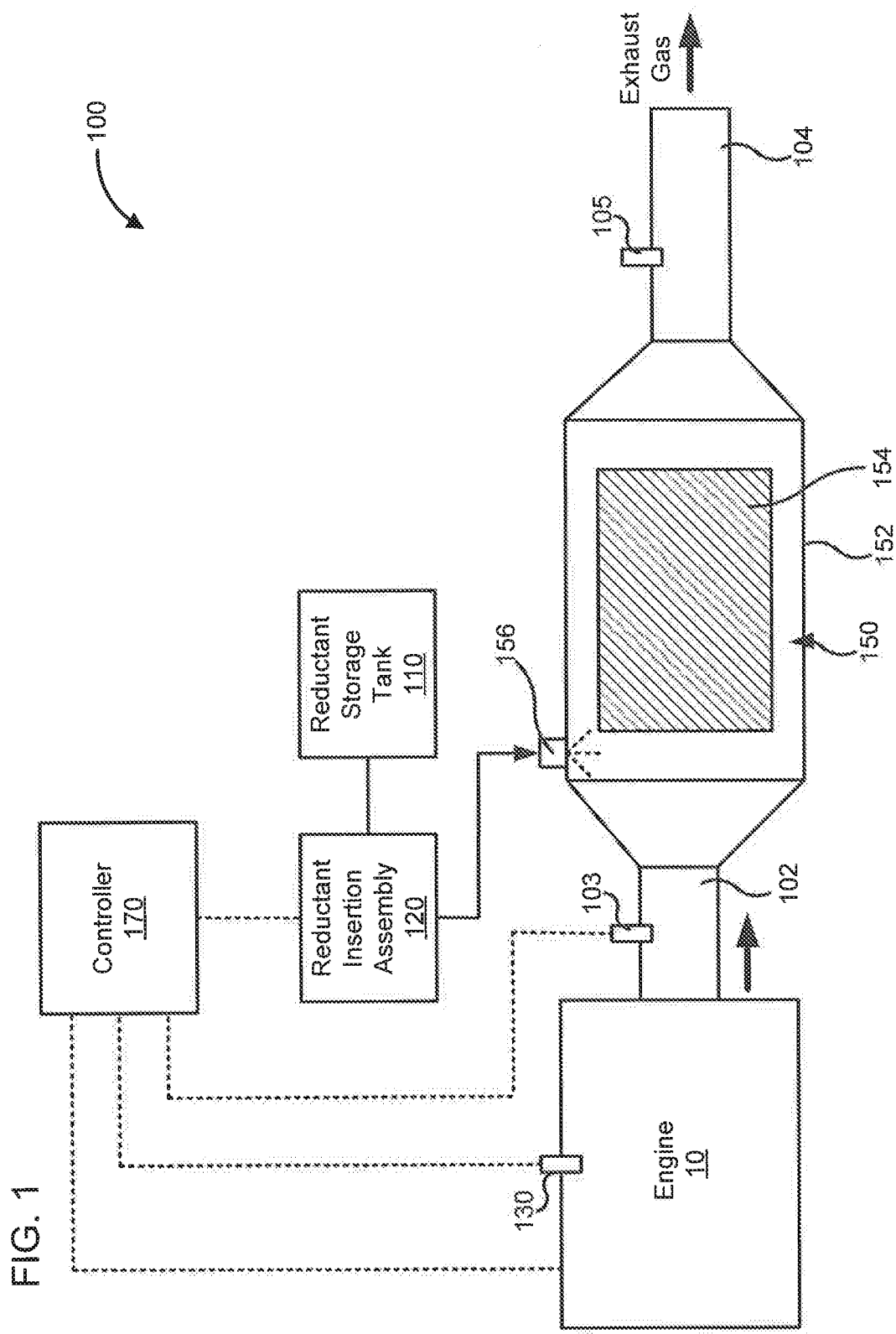
FIG. 1 is a schematic illustration of an aftertreatment system, according to an embodiment.

Reference is made to the accompanying drawings throughout the following detailed description. In the drawings, similar symbols typically identify similar components unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein and illustrated in the figures, can be arranged, substituted, combined, and designed in a wide variety of different configurations, all of which are explicitly contemplated and made part of this disclosure.

DETAILED DESCRIPTION

Embodiments described herein relate generally to systems and methods for determining an exhaust flow rate of an exhaust gas produced by an engine and, in particular, to systems and methods for determining an air-fuel ratio ("AFR") from an oxygen fraction in the exhaust gas measured by a NOx sensor, and determining the exhaust flow rate from the air-fuel ratio and a fuel rate of the engine.

Exhaust flow rate of the exhaust gas is an important parameter which may be used for determining engine efficiency, SCR design or operating parameters of the SCR system, for example the amount or frequency of reductant to be inserted into the exhaust gas. Exhaust flow rate may be estimated using various methods such as, for example the engine speed density model. However, this and other methods are not suitable for estimating exhaust flow rate in large engines, for example high horse power (HHP) engines (e.g., having a volumetric capacity in a range of 19 L to 65 L) such as those used for marine application due to complex tuning or otherwise adjustments needed to get relative accuracy. Another method includes determining exhaust flow rate using speed/torque pre-tuned table. However, this methods fails to account for changes in altitudes, engine to engine variation and flow restrictions in the aftertreatment system, for example due to plugging of a filter or a catalyst included in the aftertreatment system.

Various embodiments of the systems and methods described herein may provide benefits including, for example: (1) using an oxygen fraction measured via NOx sensor generally included in most aftertreatment systems to determine an AFR, which is used to determine the exhaust flow rate; (2) providing a simple, drop in system for determining the exhaust flow rate, which can be used in existing systems without any significant modifications; (3) overcoming inaccuracies which conventional methods cannot circumvent, such as variations in altitude, engine to engine variation and/or flow restrictions in the aftertreatment system (e.g., plugging of a filter or catalyst included in the SCR system); and (4) using actual measurements from the NOx sensor and a fuel-rate sensor for determining exhaust flow rate, thereby providing higher accuracy.

FIG. 1 is a schematic illustration of an aftertreatment system 100, according to an embodiment. The aftertreatment system 100 is configured to receive an exhaust gas from an engine 10 (e.g., a diesel engine, a gasoline engine, a natural gas engine, a dual fuel engine, a biodiesel engine, an E-85 engine, or any other suitable engine) and reduce constituents of the exhaust gas such as, for example, NOx gases, CO, hydrocarbons, etc. The aftertreatment system 100 may comprise a reductant storage tank 110, a reductant insertion assembly 120, an SCR system 150, and a controller 170.

The SCR system 150 comprises a housing 152 defining an internal volume within which at least one catalyst 154 formulated to decompose constituents of an exhaust flowing therethrough is positioned. The housing 152 may be formed from a rigid, heat-resistant and corrosion-resistant material, for example stainless steel, iron, aluminum, metals, ceramics, or any other suitable material. The housing 152 may have any suitable cross-section, for example circular, square, rectangular, oval, elliptical, polygonal, or any other suitable shape.

In some embodiments, the SCR system 150 may comprise a selective catalytic reduction filter (SCRF) system, or any other aftertreatment component configured to decompose constituents of the exhaust gas (e.g., NOx gases such as such nitrous oxide, nitric oxide, nitrogen dioxide, etc.), flowing through the aftertreatment system 100 in the presence of a reductant, as described herein.

Although FIG. 1 shows only the catalyst 154 positioned within the internal volume defined by the housing 152, in other embodiments, a plurality of aftertreatment components may be positioned within the internal volume defined by the housing 152 in addition to the catalyst 154. Such aftertreatment components may comprise, for example, filters (e.g., particulate matter filters, catalyzed filters, etc.), oxidation catalysts (e.g., carbon monoxide, hydrocarbons and/or ammonia oxidation catalysts), mixers, baffle plates, or any other suitable aftertreatment component.

An inlet conduit 102 is fluidly coupled to an inlet of the housing 152 and structured to receive exhaust gas from the engine 10 and communicate the exhaust gas to an internal volume defined by the housing 152. Furthermore, an outlet conduit 104 may be coupled to an outlet of the housing 152 and structured to expel treated exhaust gas into the environment.

A first sensor 103 is positioned in the inlet conduit 102. The first sensor 103 may comprise a NOx sensor configured to measure an amount of NOx gases included in the exhaust gas flowing into the SCR system 150. The first sensor 103 is also configured to measure an amount of oxygen included in the exhaust gas. For example, the first sensor 103 may include an electrochemical sensor. The first sensor 103 can include a catalytic element (e.g., rhodium) to catalytically decompose the NOx gases into a nitrogen gas component and an oxygen gas component. The oxygen component of the NOx gases is electrochemically reduced, for example, on a polarized electrode in an oxygen reduction reaction to yield a first output value which includes a redox current and/or voltage indicative of the amount or concentration of the oxygen component of the NOx gases. The concentration of the oxygen components corresponds to the NOx concentration of the NOx gases included in the exhaust gas and is thereby used to indirectly measure the first NOx concentration.

However, the exhaust gas generated by the engine 10 (e.g., a diesel engine) inherently includes an initial amount of oxygen or oxygen fraction. The oxygen fraction also contributes to the electrochemical redox current measured by the first sensor 103. The first sensor 103 is also configured to measure the first oxygen concentration and produce an output value indicative of the oxygen fraction as described above. For example, the first sensor 103 can include a first compartment for measuring the oxygen concentration and a second chamber for measuring the NOx concentration. At least a portion of the exhaust gas first may flow through a diffusion barrier into the first chamber which includes a simple oxygen sensor (e.g., an electrochemical oxygen sensor) for measuring the first oxygen concentration, for example via an oxygen reduction reaction. A portion of the exhaust gas also flows into the second chamber in which the first NOx concentration is measured as described before.

In various embodiments, a temperature sensor, a pressure sensor, or any other sensor may also be positioned in the inlet conduit 102 so as to determine one or more operational parameters of the exhaust gas flowing through the aftertreatment system 100. A second sensor 105 is positioned in the outlet conduit 104. The second sensor 105 may comprise a second NOx sensor configured to determine an amount of NOx gases expelled into the environment after passing through the SCR system 150. In other embodiments, the second sensor 105 may comprise an ammonia oxide (AMOx) sensor configured to measure an amount of ammonia in the exhaust gas flowing out of the SCR system 150, i.e., determine the ammonia slip. This may be used as a measure of determining a catalytic efficiency of the SCR system 150, adjust an amount of reductant to be inserted into the SCR system 150, and/or adjust a temperature of the SCR system 150 so as to allow the SCR system 150 to effectively use the ammonia for catalytic decomposition of the NOx gases included in the exhaust gas flowing therethrough.

A reductant insertion port 156 may be provided on a sidewall of housing 152 and structured to allow insertion of a reductant therethrough into the internal volume defined by the housing 152. The reductant insertion port 156 may be positioned upstream of the catalyst 154 (e.g., to allow reductant to be inserted into the exhaust gas upstream of the catalyst 154) or over the catalyst 154 (e.g., to allow reductant to be inserted directly on the catalyst 154). In other embodiments, the reductant insertion port 156 may be disposed on the inlet conduit 102 and configured to insert the reductant into the inlet conduit 102 upstream of the SCR system 150. In such embodiments, mixers, baffles, vanes or other structures may be positioned in the inlet conduit 102 so as to facilitate mixing of the reductant with the exhaust gas.

The catalyst 154 is formulated to selectively decompose constituents of the exhaust gas. Any suitable catalyst can be used such as, for example, platinum, palladium, rhodium, cerium, iron, manganese, copper, vanadium based catalyst, any other suitable catalyst, or a combination thereof. The catalyst 154 can be disposed on a suitable substrate such as, for example, a ceramic (e.g., cordierite) or metallic (e.g., kanthal) monolith core which can, for example, define a honeycomb structure. A washcoat can also be used as a carrier material for the catalyst 154. Such washcoat materials may comprise, for example, aluminum oxide, titanium dioxide, silicon dioxide, any other suitable washcoat material, or a combination thereof. The exhaust gas (e.g., diesel exhaust gas) can flow over and/or about the catalyst 154 such that any NOx gases included in the exhaust gas are further reduced to yield an exhaust gas which is substantially free of NOx gases.

The reductant storage tank 110 is structured to store a reductant. The reductant is formulated to facilitate decomposition of the constituents of the exhaust gas (e.g., NOx gases included in the exhaust gas). Any suitable reductant can be used. In some embodiments, the exhaust gas comprises a diesel exhaust gas and the reductant comprises a diesel exhaust fluid. For example, the diesel exhaust fluid may comprise urea, an aqueous solution of urea, or any other fluid that comprises ammonia, by-products, or any other diesel exhaust fluid as is known in the arts (e.g., the diesel exhaust fluid marketed under the name ADBLUE®). For example, the reductant may comprise an aqueous urea solution having a particular ratio of urea to water. In particular embodiments, the reductant can comprise an aqueous urea solution including 32.5% by volume of urea and 67.5% by volume of deionized water, including 40% by volume of urea and 60% by volume of deionize water, or any other suitable ratio of urea to deionized water.

A reductant insertion assembly 120 is fluidly coupled to the reductant storage tank 110. The reductant insertion assembly 120 is configured to selectively insert the reductant into the SCR system 150 or upstream thereof (e.g., into the inlet conduit 102) or a mixer (not shown) positioned upstream of the SCR system 150. The reductant insertion assembly 120 may comprise various structures to facilitate receipt of the reductant from the reductant storage tank 110 and delivery to the SCR system 150.

For example, the reductant insertion assembly 120 may comprise one or more pumps having filter screens (e.g., to prevent solid particles of the reductant or contaminants from flowing into the pump) and/or valves (e.g., check valves) positioned upstream thereof to receive reductant from the reductant storage tank 110. In some embodiments, the pump may comprise a diaphragm pump but any other suitable pump may be used such as, for example, a centrifugal pump, a suction pump, etc.

The pump may be configured to pressurize the reductant so as to provide the reductant to the SCR system 150 at a predetermined pressure. Screens, check valves, pulsation dampers, or other structures may also be positioned downstream of the pump to provide the reductant to the SCR system 150. In various embodiments, the reductant insertion assembly 120 may also comprise a bypass line structured to provide a return path of the reductant from the pump to the reductant storage tank 110.

A valve (e.g., an orifice valve) may be provided in the bypass line. The valve may be structured to allow the reductant to pass therethrough to the reductant storage tank 110 if an operating pressure of the reductant generated by the pump exceeds a predetermined pressure so as to prevent over pressurizing of the pump, the reductant delivery lines, or other components of the reductant insertion assembly 120. In some embodiments, the bypass line may be configured to allow the return of the reductant to the reductant storage tank 110 during purging of the reductant insertion assembly 120 (e.g., after the aftertreatment system 100 is shut off).

In various embodiments, the reductant insertion assembly 120 may also comprise a blending chamber structured to receive pressurized reductant from a metering valve at a controllable rate. The blending chamber may also be structured to receive air (e.g., compressed air or portion of the exhaust gas), or any other inert gas (e.g., nitrogen), for example from an air supply unit so as to deliver a combined flow of the air and the reductant to the SCR system 150 through the reductant insertion port 156. In various embodiments, a nozzle may be positioned in the reductant insertion port 156 and structured to deliver a stream or a jet of the reductant into the internal volume of the housing 152 so as to deliver the reductant to the catalyst 154 of the SCR system 150.

In various embodiments, the reductant insertion assembly 120 may also comprise a dosing valve, for example positioned within a reductant delivery line for delivering the reductant from the reductant insertion assembly 120 to the SCR system 150. The dosing valve can comprise any suitable valve, for example a butterfly valve, a gate valve, a check valve (e.g., a tilting disc check valve, a swing check valve, an axial check valve, etc.), a ball valve, a spring loaded valve, an air assisted injector, a solenoid valve, or any other suitable valve. The dosing valve may be selectively opened to insert a predetermined quantity of the reductant for a predetermined time into the SCR system 150 or upstream therefrom.

The controller 170 is communicatively coupled to the first sensor 103 and is configured to receive a first sensor signal from the first sensor 103. The first sensor signal is indicative of an amount of oxygen in the exhaust gas produced by the engine 10 and entering the SCR system 150. The signal may comprise, for example a voltage or a current (e.g., a redox current associated with the oxygen reduction reaction). The controller 170 is also configured to receive a fuel rate signal corresponding to a rate of fuel consumption by the engine 10. For example, a fuel rate sensor 130 may be operably coupled to the engine 10 and generate the fuel rate signal indicative of the fuel rate. The controller 170 may be communicatively coupled to the fuel rate sensor 130 and configured to receive the fuel rate signal therefrom. In other embodiments, the controller 170 may be communicatively coupled to a fuel insertion system of the engine 10 and configured to receive the fuel rate signal therefrom. The fuel rate signal may correspond to a rate of fuel consumption by the engine 10, or otherwise a rate of fuel inserted into the engine 10, and the controller 170 may be configured to interpret the fuel rate signal so as to determine the fuel rate therefrom.

The controller 170 may be operably coupled to the first sensor 103, the fuel rate sensor 130 and/or other components of the engine 10, or a vehicle including the engine 10 using any type and any number of wired or wireless connections. For example, a wired connection may include a serial cable, a fiber optic cable, a CAT5 cable, or any other form of wired connection. Wireless connections may include the Internet, Wi-Fi, cellular, radio, Bluetooth, ZigBee, etc. In one embodiment, a controller area network (CAN) bus provides the exchange of signals, information, and/or data. The CAN bus includes any number of wired and wireless connections.

The controller 170 is configured to determine an AFR from the first sensor signal. For example, the controller 170 may be configured to determine an oxygen fraction in the exhaust gas from the first sensor signal, and determine the air-fuel ratio from the oxygen fraction. In particular embodiments, the controller 170 may be configured determine a stoichiometric coefficient comprising a ratio of the air-fuel ratio to a stoichiometric air-fuel ratio from the oxygen fraction, and determine the air-fuel ratio from the stoichiometric coefficient. In still other embodiments, the oxygen fraction may comprise an oxygen molar fraction. The controller 170 may be configured to determine an oxygen mass fraction from the oxygen molar fraction, and determine the air-fuel ratio from the oxygen mass fraction.

Expanding further, the combustion of a hydrocarbon fuel (e.g., diesel or gasoline) inserted into the engine 10 may be represented by the following equation:

$$C_xH_y + a(1+\lambda)(O_2 + 3.76N_2) \rightarrow xCO_2 + \frac{y}{2}H_2O + \lambda aO_2 + 3.76a(1+\lambda)N_2 \quad (1)$$

where $C_xH_y$ is the chemical formula of the hydrocarbon fuel, $\Lambda$ is the stoichiometric air-fuel ratio, and $a=x+y/4$.

The oxygen ($O_2$) fraction in the exhaust gas is represented by the following equation:

$$O_2\text{Fraction} = \frac{\lambda a}{x + \frac{y}{2} + \lambda a + 3.76a(1+\lambda)} \quad (2)$$

The oxygen fraction is determined from the first sensor signal generated by the first sensor 103, as previous described herein. Thus, A may be determined using equation (2). The controller 170 may be configured to correct the first sensor signal received from the first sensor 103 (e.g., using a correction factor, for example the amount of NOx in the exhaust gas), and/or filter the first sensor signal, for example to remove any noise in the first sensor signal. The controller 170 may also be configured to determine the AFR using the following equation:

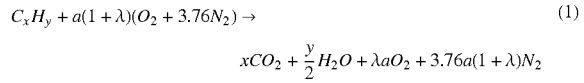

$$AFR = \frac{a(1+\lambda)*4.76}{1} \times \frac{MW_{air}}{MW_{fuel}} \quad (3)$$

where $MW_{air}$ is the molecular weight of air and $MW_{fuel}$ is the molecular weight of the fuel (e.g., diesel, gasoline, natural gas, ethanol, methanol, bio-diesel, etc.).

The controller 170 is also configured to determine a fuel rate from the fuel rate signal. The controller 170 is configured to determine the exhaust flow rate from the fuel rate and the AFR. For example, the controller 170 may use the following equation to determine the exhaust flow rate:

$$\text{Exhaust Flow} = (1+AFR) \times \text{Fuel Rate} \quad (4)$$

In this manner, the controller 170 uses oxygen fraction measurements from the first sensor 103 (e.g., a NOx sensor) and a fuel rate measurements from the fuel rate sensor 130 to accurately determine the exhaust flow rate, irrespective of variations in altitude, engine-to-engine variations or flow restrictions in the aftertreatment system 100. The controller 170 may be configured to generate an exhaust flow rate signal indicative of the exhaust flow rate. The controller 170 may be configured to store an exhaust flow rate value in a memory thereof which may be updated in real time and/or communicate the exhaust flow rate signal or value thereof to a central controller (e.g., an engine control unit). In some embodiments, the controller 170 may also be communicatively coupled to the reductant insertion assembly 120 and configured to adjust an amount of the reductant inserted by the reductant insertion assembly 120 into the SCR system 150 based on the determine exhaust flow rate. For example, the controller 170 may be configured to generate a reductant insertion signal configured to cause the reductant insertion assembly 120 to adjust the amount of the reductant to be inserted into the SCR system 150. Since the amount of reductant to be inserted into the exhaust gas for efficient reduction of the NOx gases is also dependent upon the exhaust flow rate, accurate determining of the exhaust flow rate using the methods described herein allows determination and insertion of a more accurate amount of reductant into the exhaust gas. This may lead to achieving an optimal catalytic conversion efficiency of the SCR system 150 and reducing ammonia slip.

In some embodiments, the controller 170 or the central controller may be used to determine an operating condition of the engine 10 and adjust the one or more engine operating parameters (e.g., engine speed, engine torque, fuel rate, air-fuel insertion timing, spark ignition timing, etc.) based on the determined exhaust flow rate, so as to obtain a desired exhaust flow rate. For example, the controller 170 may also be communicatively coupled to the engine 10 and configured to generate an operating parameter adjustment signal configured to adjust at least one engine operating parameter based on the exhaust flow rate. In particular arrangements, the determined exhaust flow rate may also be used as a correction factor for adjusting an exhaust flow rate determined using any other methods, for example the engine speed density model, a speed/torque table, or a flow rate sensor.

Figure 2:
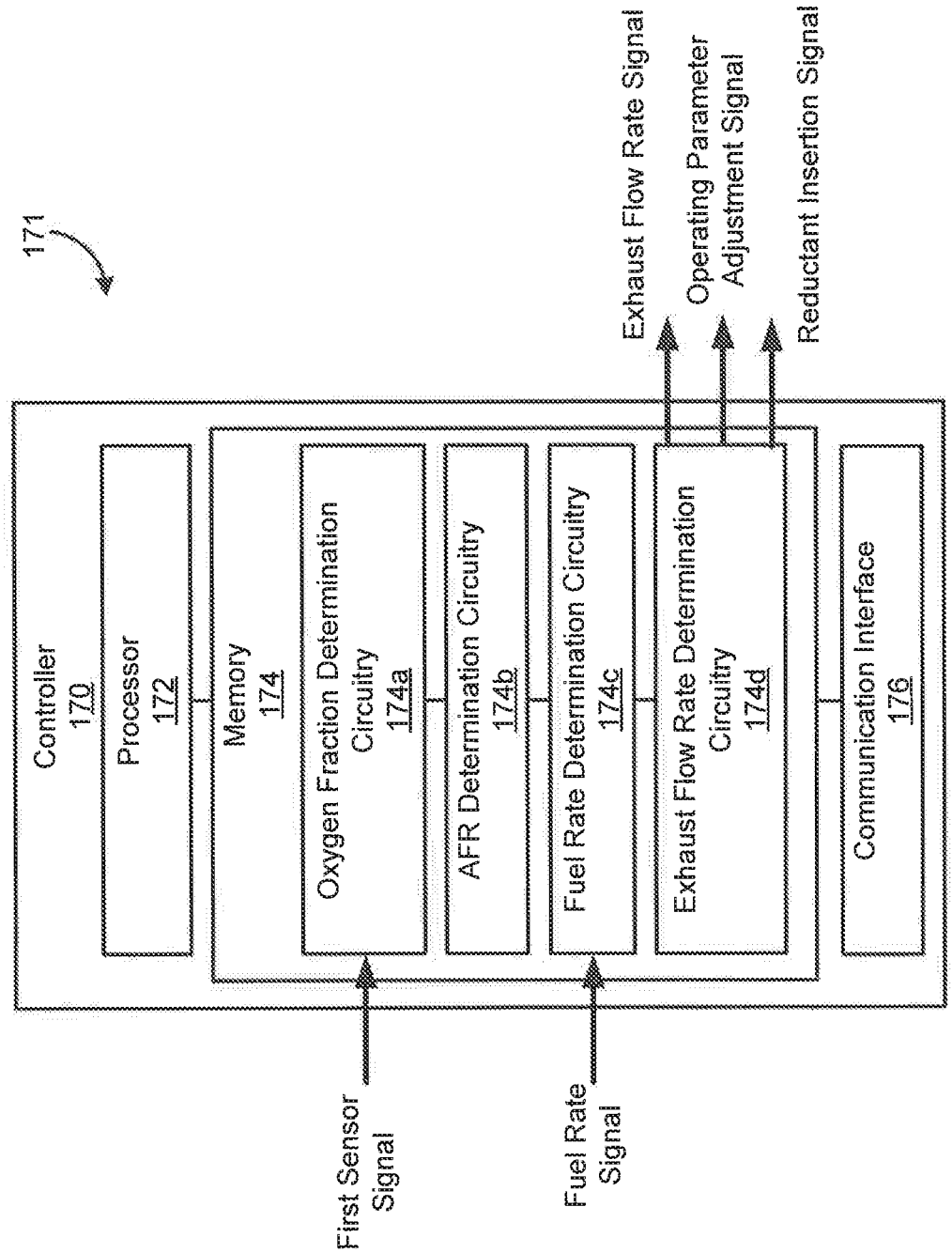
FIG. 2 is a schematic block diagram of an embodiment of a control circuitry that may be included in the aftertreatment system of FIG. 1.

In particular embodiments, the controller 170 can be included in a control circuitry. For example, FIG. 2 is a schematic block diagram of a control circuitry 171 that comprises the controller 170, according to an embodiment. The controller 170 comprises a processor 172, a memory 174, or any other computer readable medium, and a communication interface 176. Furthermore, the controller 170 includes an oxygen fraction determination circuitry 174*a*, an AFR determination circuitry 174*b*, a fuel rate determination circuitry 174*c* and an exhaust flow rate determination circuitry 174*d*. It should be understood that the controller 170 shows only one embodiment of the controller 170 and any other controller capable of performing the operations described herein can be used.

The processor 172 can comprise a microprocessor, programmable logic controller (PLC) chip, an ASIC chip, or any other suitable processor. The processor 172 is in communication with the memory 174 and configured to execute instructions, algorithms, commands, or otherwise programs stored in the memory 174.

The memory 174 comprises any of the memory and/or storage components discussed herein. For example, memory 174 may comprise a RAM and/or cache of processor 172. The memory 174 may also comprise one or more storage devices (e.g., hard drives, flash drives, computer readable media, etc.) either local or remote to controller 170. The memory 174 is configured to store look up tables, algorithms, or instructions.

In one configuration, the oxygen fraction determination circuitry 174*a*, the AFR determination circuitry 174*b*, the fuel rate determination circuitry 174*c* and the exhaust flow rate determination circuitry 174*d* are embodied as machine or computer-readable media (e.g., stored in the memory 174) that is executable by a processor, such as the processor 172. As described herein and amongst other uses, the machine-readable media (e.g., the memory 174) facilitates performance of certain operations to enable reception and transmission of data. For example, the machine-readable media may provide an instruction (e.g., command, etc.) to, e.g., acquire data. In this regard, the machine-readable media may include programmable logic that defines the frequency of acquisition of the data (or, transmission of the data). Thus, the computer readable media may include code, which may be written in any programming language including, but not limited to, Java or the like and any conventional procedural programming languages, such as the "C" programming language or similar programming languages. The computer readable program code may be executed on one processor or multiple remote processors. In the latter scenario, the remote processors may be connected to each other through any type of network (e.g., CAN bus, etc.).

In another configuration, the oxygen fraction determination circuitry 174*a*, the AFR determination circuitry 174*b*, the fuel rate determination circuitry 174*c* and the exhaust flow rate determination circuitry 174*d* are embodied as hardware units, such as electronic control units. As such, the oxygen fraction determination circuitry 174*a*, the AFR determination circuitry 174*b*, the fuel rate determination circuitry 174*c* and the exhaust flow rate determination circuitry 174*d* may be embodied as one or more circuitry components including, but not limited to, processing circuitry, network interfaces, peripheral devices, input devices, output devices, sensors, etc.

In some embodiments, the oxygen fraction determination circuitry 174*a*, the AFR determination circuitry 174*b*, the fuel rate determination circuitry 174*c* and the exhaust flow rate determination circuitry 174*d* may take the form of one or more analog circuits, electronic circuits (e.g., integrated circuits (IC), discrete circuits, system on a chip (SOCs) circuits, microcontrollers, etc.), telecommunication circuits, hybrid circuits, and any other type of "circuit." In this regard, the oxygen fraction determination circuitry 174*a*, the AFR determination circuitry 174*b*, the fuel rate determination circuitry 174*c* and the exhaust flow rate determination circuitry 174*d* may include any type of component for accomplishing or facilitating achievement of the operations described herein. For example, a circuit as described herein may include one or more transistors, logic gates (e.g., NAND, AND, NOR, OR, XOR, NOT, XNOR, etc.), resistors, multiplexers, registers, capacitors, inductors, diodes, wiring, and so on.

Thus, the oxygen fraction determination circuitry 174*a*, the AFR determination circuitry 174*b*, the fuel rate determination circuitry 174*c* and the exhaust flow rate determination circuitry 174*d* may also include programmable hardware devices such as field programmable gate arrays, programmable array logic, programmable logic devices or the like. In this regard, the oxygen fraction determination circuitry 174*a*, the AFR determination circuitry 174*b*, the fuel rate determination circuitry 174*c* and the exhaust flow rate determination circuitry 174*d* may include one or more memory devices for storing instructions that are executable by the processor(s) of the oxygen fraction determination circuitry 174*a*, the AFR determination circuitry 174*b*, the fuel rate determination circuitry 174*c* and the exhaust flow rate determination circuitry 174*d*. The one or more memory devices and processor(s) may have the same definition as provided below with respect to the memory 174 and the processor 172.

In the example shown, the controller 170 includes the processor 172 and the memory 174. The processor 172 and the memory 174 may be structured or configured to execute or implement the instructions, commands, and/or control processes described herein with respect the oxygen fraction determination circuitry 174a, the AFR determination circuitry 174b, the fuel rate determination circuitry 174c and the exhaust flow rate determination circuitry 174d. Thus, the depicted configuration represents the aforementioned arrangement where the oxygen fraction determination circuitry 174a, the AFR determination circuitry 174b, the fuel rate determination circuitry 174c and the exhaust flow rate determination circuitry 174d are embodied as machine or computer-readable media. However, as mentioned above, this illustration is not meant to be limiting as the present disclosure contemplates other embodiments such as the aforementioned embodiment where the oxygen fraction determination circuitry 174a, the AFR determination circuitry 174b, the fuel rate determination circuitry 174c and the exhaust flow rate determination circuitry 174d, or at least one circuit of the oxygen fraction determination circuitry 174a, the AFR determination circuitry 174b, the fuel rate determination circuitry 174c and the exhaust flow rate determination circuitry 174d are configured as a hardware unit. All such combinations and variations are intended to fall within the scope of the present disclosure.

The processor 172 may be implemented as one or more general-purpose processors, an application specific integrated circuit (ASIC), one or more field programmable gate arrays (FPGAs), a digital signal processor (DSP), a group of processing components, or other suitable electronic processing components. In some embodiments, the one or more processors may be shared by multiple circuits (e.g., the oxygen fraction determination circuitry 174a, the AFR determination circuitry 174b, the fuel rate determination circuitry 174c and the exhaust flow rate determination circuitry 174d) may comprise or otherwise share the same processor which, in some example embodiments, may execute instructions stored, or otherwise accessed, via different areas of memory). Alternatively or additionally, the one or more processors may be structured to perform or otherwise execute certain operations independent of one or more co-processors. In other example embodiments, two or more processors may be coupled via a bus to enable independent, parallel, pipelined, or multi-threaded instruction execution. All such variations are intended to fall within the scope of the present disclosure. The memory 174 (e.g., RAM, ROM, Flash Memory, hard disk storage, etc.) may store data and/or computer code for facilitating the various processes described herein. The memory 174 may be communicably connected to the processor 172 to provide computer code or instructions to the processor 172 for executing at least some of the processes described herein. Moreover, the memory 174 may be or include tangible, non-transient volatile memory or non-volatile memory. Accordingly, the memory 174 may include database components, object code components, script components, or any other type of information structure for supporting the various activities and information structures described herein.

The communication interface 176 may include wireless interfaces (e.g., jacks, antennas, transmitters, receivers, communication interfaces, wire terminals, etc.) for conducting data communications with various systems, devices, or networks. For example, the communication interface 176 may include an Ethernet card and port for sending and receiving data via an Ethernet-based communications network and/or a Wi-Fi communication interface for communicating with the first sensor 103 and the fuel rate sensor 130, or another controller (e.g., an engine control unit). The communication interface 176 may be structured to communicate via local area networks or wide area networks (e.g., the Internet, etc.) and may use a variety of communications protocols (e.g., IP, LON, Bluetooth, ZigBee, radio, cellular, near field communication, etc.).

The oxygen fraction determination circuitry 174a is configured to receive the first sensor signal from the first sensor 103, and determine the oxygen fraction therefrom. The oxygen fraction determination circuitry 174a may also be configured to filter the raw first sensor signal received from the first sensor 103. In particular embodiments, the oxygen fraction determination circuitry 174a may be configured to determine an oxygen molar fraction from the first sensor signal. The oxygen molar fraction may then be used to determine an oxygen mass fraction using the molecular weight of oxygen ($MW_{O2}$) and the molecular weight of the exhaust gas ($MW_{exh}$), which may be used to determine the AFR.

The AFR determination circuitry 174b is configured to determine the AFR using the oxygen fraction determined by the oxygen fraction determination circuitry 174a. For example, the AFR determination circuitry 174b may use equation (2) and equation (3) as previously described herein, or any other equation or algorithm described herein to determine the AFR.

The fuel rate determination circuitry 174c is configured to receive a fuel rate signal and determine the fuel rate therefrom. For example, the fuel rate determination circuitry 174c may be configured to receive the fuel rate signal from the fuel rate sensor 130, or any other sensor or circuitry generating the fuel rate signal and determine the fuel rate therefrom.

The exhaust flow rate determination circuitry 174d is configured to determine the exhaust flow rate using the fuel rate and the AFR. For example, the exhaust flow rate determination circuitry 174d may use the AFR and the fuel rate to determine the exhaust flow rate using equation (4) or any other equation or algorithm described herein. The exhaust flow rate determination circuitry 174d may also generate an exhaust flow rate signal indicative of the exhaust flow rate. In some embodiments, the exhaust flow rate determination circuitry 174d may be configured to communicate the exhaust flow rate signal or otherwise, an exhaust flow rate value determined from the exhaust flow rate signal to a central controller (e.g., an engine control unit), for example to store in a memory thereof. In some embodiments, the exhaust flow rate determination circuitry 174d may be configured to generate a reductant insertion signal communicated to the reductant insertion assembly 120, and configured to cause the reductant insertion assembly 120 to adjust an amount of reductant inserted into the SCR system 150. In other embodiments, the exhaust flow rate value may be used as a correction factor for adjusting a measured exhaust flow rate, or to adjust an operating parameter of the engine 10 and/or the reductant insertion assembly 120. For example, the controller 170 may also be communicatively coupled to the engine 10 via the communication interface 176. The exhaust flow rate determination circuitry 174d may also be configured to generate an operating parameter adjustment signal communicated to the engine 10 and configured to cause the engine 10 to adjust at least one engine operating parameter thereof based on the determined exhaust flow rate.

Figure 3:
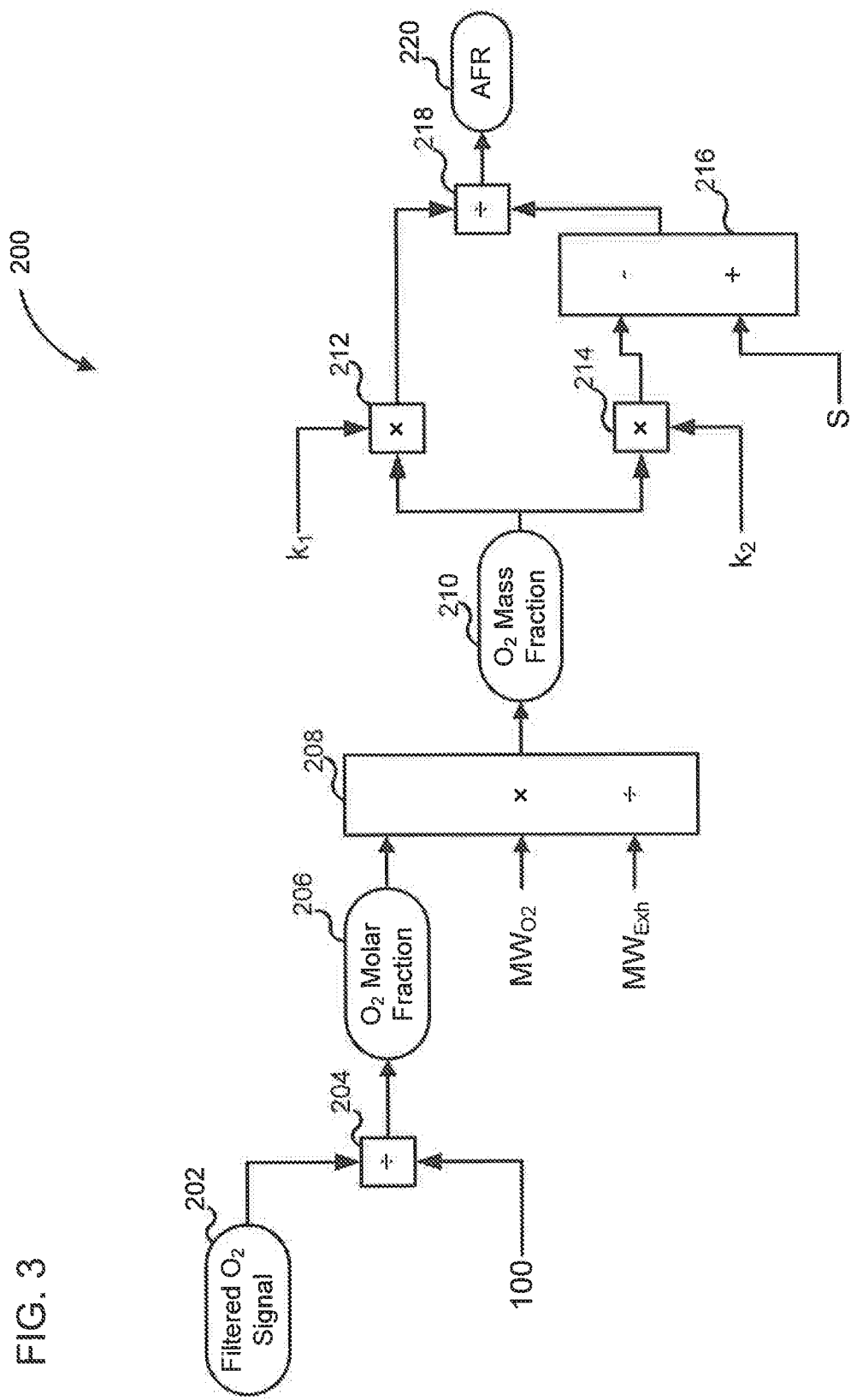
FIG. 3 is a schematic block diagram of an example process which may be used by the controller of FIG. 1 to determine an exhaust flow rate of an exhaust gas produced by an engine.

FIG. 3 is a schematic flow diagram of a process 200 for determining the exhaust flow rate of the exhaust gas produced by an engine (e.g., the engine 10), according to a particular embodiment. The process 200 may be implemented with the controller 170, the control circuitry 171 or any other controller described herein. A filtered oxygen signal 202, for example the first sensor signal generated by the first sensor 103 and filtered by the oxygen fraction determination circuitry 174a, is received at a first operation block 204, and divided by 100 to determine an oxygen molar fraction 206. The oxygen molar fraction is multiplied with the molecular weight of oxygen ($MW_{O2}$), and divided by the molecular weight of the exhaust gas ($MW_{exh}$) at block 208 so as to determine the oxygen mass fraction ($M_{O2}$) 210.

The oxygen mass fraction 210 is multiplied by $k_1$ at block 212, and multiplied by $k_2$ at block 214, where:

$$k_1 = x + \frac{y}{2} + a \times 3.76, \quad (5)$$

$$k_2 = a \times 4.76, \quad (6)$$

$$a = x + \frac{y}{4}, \quad (7)$$

x is the number of atoms of carbon and y is the number of atoms of hydrogen included in the fuel used in the combustion reaction by the engine 10.

At block 216, the multiple of $k_2$ and $M_{O2}$ is subtracted from the stoichiometric AFR ("S") at block 216 and divided from the multiple of $k_1$ and $M_{O2}$ at block 218 to determine the AFR 220, according to the following equation:

$$AFR = \frac{k_1 M_{O2}}{S - k_2 M_{O2}}. \quad (8)$$

Figure 4:
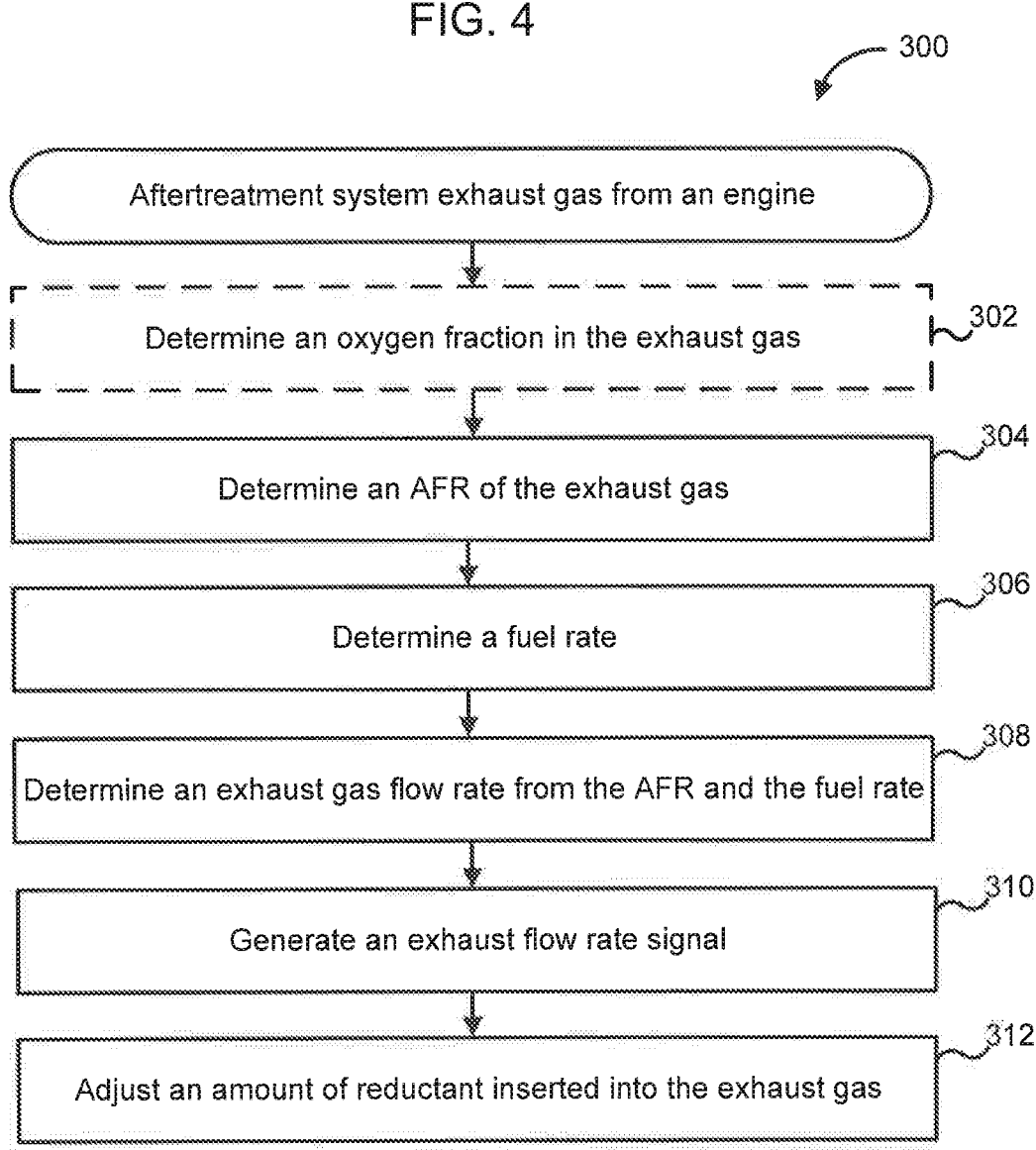
FIG. 4 is a schematic flow diagram of a method for determining an exhaust flow rate using an AFR and a fuel rate, according to an embodiment.

FIG. 4 is a schematic flow diagram of an example method 300 for determining an exhaust flow rate of an exhaust gas produced by an engine (e.g., the engine 10). The engine may be fluidly coupled to an aftertreatment system (e.g., the aftertreatment system 100) and configured to receive the exhaust gas from the engine and decompose constituents of the exhaust gas, for example NOx gases included in the exhaust gas.

In some embodiments, the method 300 comprises determining an oxygen fraction in the exhaust gas, at 302. For example, the first sensor 103 generates a first sensor signal indicative of the oxygen fraction. The controller 170 (e.g., the oxygen fraction determination circuitry 174a) may be configured to interpret the first sensor signal and determine the oxygen fraction therefrom, as previously described in detail herein.

An AFR of the exhaust gas is determined, at 304. For example, the controller 170 (e.g., the AFR determination circuitry 174b) may determine the AFR from the oxygen fraction using the equations (2) and (3), or equations (5) to (8), as previous described herein. In some embodiments, the method 300 may also include determining a stoichiometric coefficient including a ratio of the AFR to a stoichiometric AFR from the oxygen fraction, and the AFR is determined from the stoichiometric coefficient. In other embodiments in which the oxygen fraction includes an oxygen molar fraction, the method 300 may include determining an oxygen mass fraction from the oxygen molar fraction, and the AFR is determined from the oxygen mass fraction.

A fuel rate corresponding to a rate of consumption of a fuel by the engine is determined, at 306. For example, the controller 170 (e.g., the fuel rate determination circuitry 174c) may be configured to receive a fuel rate signal generated by the fuel rate sensor 130, or any other fuel rate signal, and interpret the fuel rate signal so as to determine the fuel rate.

An exhaust flow rate is determined from the AFR and the fuel rate, at 308. For example, the controller 170 (e.g., the exhaust flow rate determination circuitry 174d) may be configured to determine the exhaust flow rate from the AFR and the fuel rate using equation (4), as previously described herein. An exhaust flow rate signal is generated, at 310. For example, the controller 170 (e.g., the exhaust flow rate determination circuitry 174d) may be configured to generate the exhaust flow rate signal indicative of the exhaust flow rate. The exhaust flow rate signal or otherwise, an exhaust flow rate value may be communicated to a central controller (e.g., an engine control unit), for example to store in a memory thereof. The exhaust flow rate signal or value may be used as a correction factor for adjusting a measured exhaust flow rate, or to adjust an operating parameter of the engine 10 and/or the reductant insertion assembly 120.

In some embodiments, an amount of reductant inserted into the exhaust gas is adjusted based on the determined exhaust flow rate, at 312. For example, the controller 170 (e.g., the exhaust flow determination circuitry 174d) may also be communicatively coupled to the reductant insertion assembly 120, and configured to generate a reductant insertion signal. The reductant insertion signal may be configured to cause the reductant insertion assembly to adjust the amount of reductant inserted into the SCR system 150 based on the determined exhaust flow rate.

Figure 5:
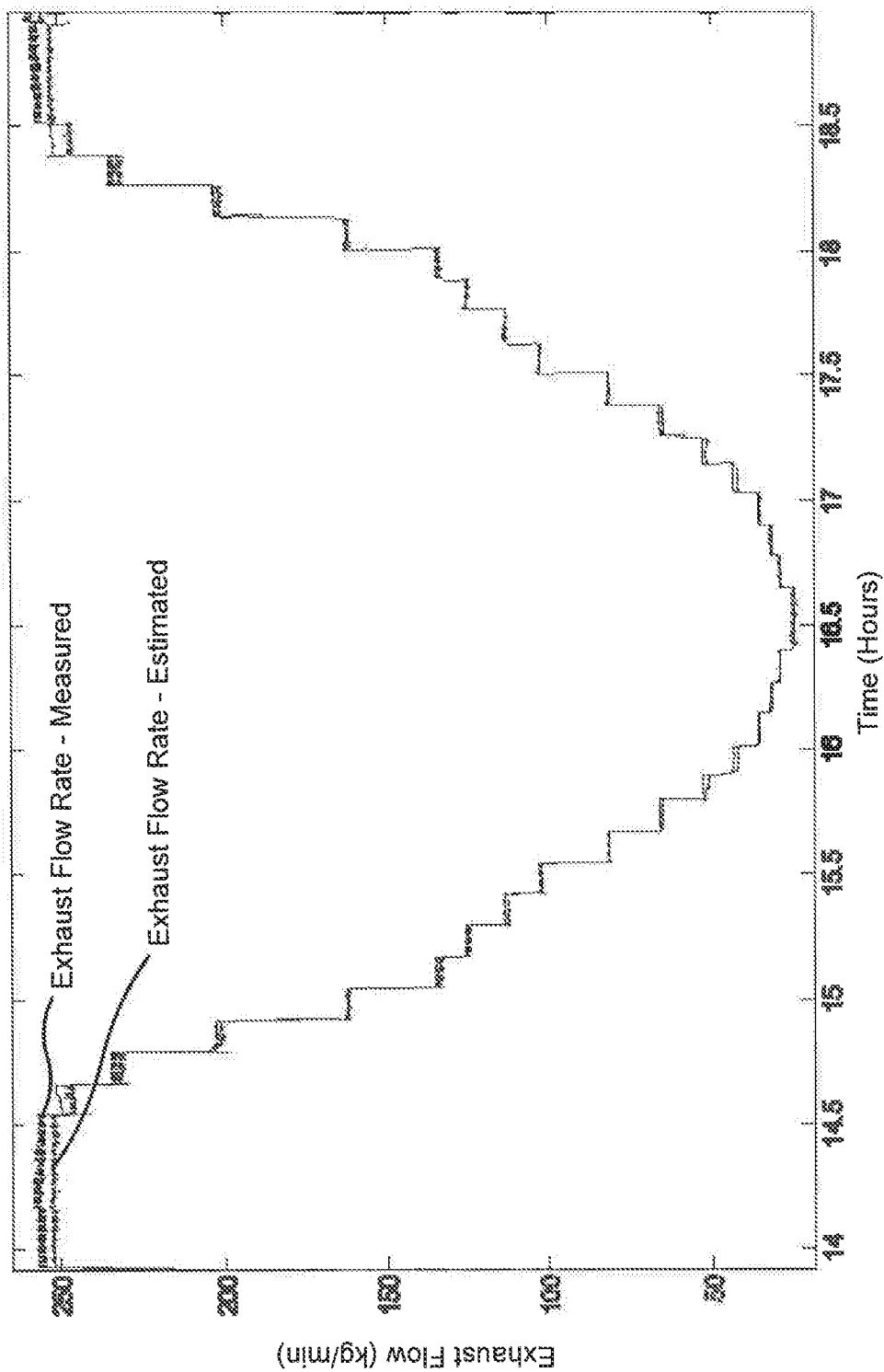
FIG. 5 is a plot showing the comparison of a measured exhaust flow rate of an exhaust gas produced by an engine and an estimated exhaust flow rate determined using the method of FIG. 4.

FIG. 5 is a plot of an exhaust flow rate of an exhaust gas produced by an engine measured using a flow rate sensor, and an estimated exhaust flow rate of the engine determined using an oxygen fraction measured by a NOx sensor, and a fuel rate corresponding to rate of consumption of a fuel by the engine, according to the methods described herein. Close correlation is observed between the measured exhaust flow rate and the estimated exhaust flow rate, thereby demonstrating the accuracy of the methods described herein for the determining the exhaust flow rate of exhaust gases produced by an engine, for example the engine 10 or any other IC engine.

Figure 6:
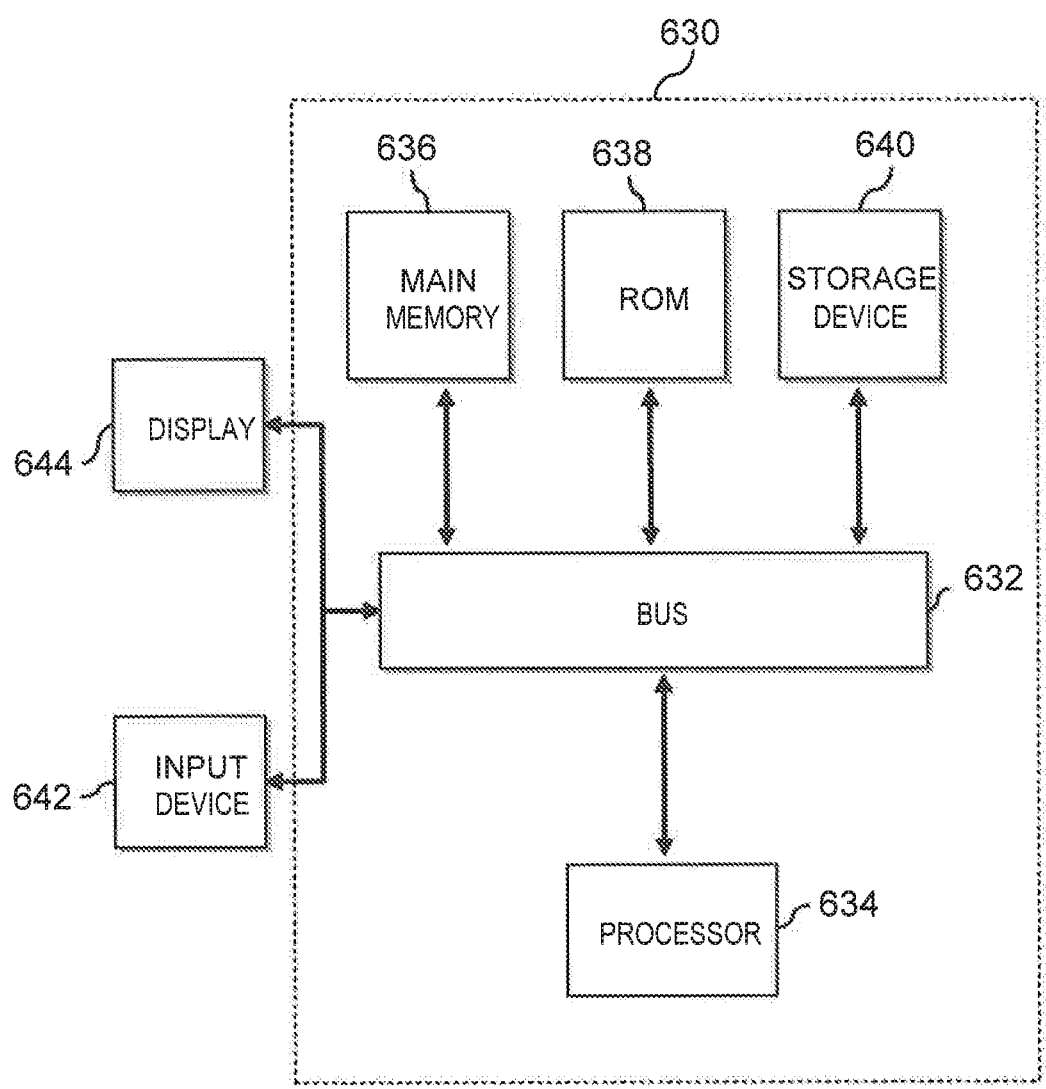
FIG. 6 is a schematic block diagram of a computing device which may be used as the controller shown in FIGS. 1 and/or 2.

In some embodiments, the controller 170, the control circuitry 171, or any of the controller or control circuitries described herein can comprise a system computer of an apparatus or system which comprises the aftertreatment system 100 (e.g., a vehicle, an engine or generator set, etc.). For example, FIG. 6 is a block diagram of a computing device 630 in accordance with an illustrative implementation. The computing device 630 can be used to perform any of the methods or the processes described herein, for example the process 200 or the method 300. In some embodiments, the controller 170 can comprise the computing device 630. The computing device 630 comprises a bus 632 or other communication component for communicating information. The computing device 630 can also comprise one or more processors 634 or processing circuits coupled to the bus 632 for processing information.

The computing device 630 also comprises main memory 636, such as a random access memory (RAM) or other dynamic storage device, coupled to the bus 632 for storing information and instructions to be executed by the processor 634. Main memory 636 can also be used for storing position information, temporary variables, or other intermediate information during execution of instructions by the processor 634. The computing device 630 may further comprise ROM 638 or other static storage device coupled to the bus 632 for storing static information and instructions for the processor 634. A storage device 640, such as a solid-state device, magnetic disk or optical disk, is coupled to the bus 632 for persistently storing information and instructions. For example, instructions corresponding operations of the process 200 or method 300 can be stored on the storage device 640.

The computing device 630 may be coupled via the bus 632 to a display 644, such as a liquid crystal display or active matrix display, for displaying information to a user. An input device 642, such as a keyboard or alphanumeric pad, may be coupled to the bus 632 for communicating information and command selections to the processor 634. In another implementation, the input device 642 has a touch screen display 644.

According to various implementations, the processes and methods described herein can be implemented by the computing device 630 in response to the processor 634 executing an arrangement of instructions contained in main memory 636 (e.g., the operations of the process 200 or method 300). Such instructions can be read into main memory 636 from another non-transitory computer-readable medium, such as the storage device 640. Execution of the arrangement of instructions contained in main memory 636 causes the computing device 630 to perform the illustrative processes described herein. One or more processors in a multi-processing arrangement may also be employed to execute the instructions contained in main memory 636. In alternative implementations, hard-wired circuitry may be used in place of or in combination with software instructions to effect illustrative implementations. Thus, implementations are not limited to any specific combination of hardware and software.

Although an example computing device has been described in FIG. 6, implementations described in this specification can be implemented in other types of digital electronic, or in computer software, firmware, or hardware, including the structures disclosed in this specification and their structural equivalents, or in combinations of one or more of them.

Implementations described in this specification can be implemented in digital electronic, or in computer software, firmware, or hardware, including the structures disclosed in this specification and their structural equivalents, or in combinations of one or more of them. The implementations described in this specification can be implemented as one or more computer programs (i.e., one or more circuitries of computer program instructions) encoded on one or more computer storage media for execution by, or to control the operation of, data processing apparatus. A computer storage medium comprises a non-transitory computer readable medium and can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate components or media (e.g., multiple CDs, disks, or other storage devices). Accordingly, the computer storage medium is both tangible and non-transitory.

The operations described in this specification can be performed by a data processing apparatus on data stored on one or more computer-readable storage devices or received from other sources. The term "data processing apparatus" or "computing device" encompasses all kinds of apparatus, devices, and machines for processing data, including, by way of example, a programmable processor, a computer, a system on a chip, or multiple ones, or combinations of the foregoing. The apparatus can comprise special purpose logic, e.g., an FPGA (field programmable gate array) or an ASIC (application-specific integrated circuit). In addition to hardware, the apparatus can also comprise code that creates an execution environment for the computer program in question (e.g., code that constitutes processor firmware, a protocol stack, a database management system, an operating system, a cross-platform runtime environment, a virtual machine, or a combination of one or more of them). The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a circuitry, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more circuitries, sub-programs, or portions of code). A computer program can be deployed to be executed on one computer, on multiple computers that are located at one site, or distributed across multiple sites and interconnected by a communication network.

Processors suitable for the execution of a computer program comprise, by way of example, both general and special purpose microprocessors and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also comprise, or be operatively coupled to receive data from or transfer data to, or both, one or more mass storage devices for storing data (e.g., magnetic, magneto-optical disks, or optical disks). However, a computer need not have such devices. Devices suitable for storing computer program instructions and data comprise all forms of non-volatile memory, media and memory devices, including, by way of example, semiconductor memory devices (e.g., EPROM, EEPROM, and flash memory devices); magnetic disks (e.g., internal hard disks or removable disks); magneto-optical disks; and CD-ROM and DVD-ROM disks. The processor and the memory can be supplemented by, or incorporated in, special purpose logic.

It should be noted that the term "example" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected" and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements; values of parameters, mounting arrangements; use of materials, colors, orientations, etc.) without materially departing from the novel teachings and advantages of the subject matter described herein. Additionally, it should be understood that features from one embodiment disclosed herein may be combined with features of other embodiments disclosed herein as one of ordinary skill in the art would understand. Other substitutions, modifications, changes, and omissions may also be made in the design, operating conditions, and arrangement of the various exemplary embodiments without departing from the scope of the present embodiments.

While this specification contains many specific implementation details, these should not be construed as limitations on the scope of any embodiments or of what may be claimed, but rather as descriptions of features specific to particular implementations of particular embodiments. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A system for determining an exhaust flow rate of an exhaust gas produced by an engine, comprising:
   a first sensor comprising a NOx sensor configured to measure an amount of NOx gases in the exhaust gas, the first sensor further configured to measure an amount of oxygen included in the exhaust gas; and
   a controller communicatively coupled to the first sensor, the controller configured to:
   receive a first sensor signal from the first sensor;
   receive a fuel rate signal corresponding to a rate of fuel consumption by the engine;
   determine an oxygen fraction in the exhaust gas from the first sensor signal;
   determine an air-fuel ratio from the oxygen fraction;
   determine a fuel rate from the fuel rate signal; and
   determine the exhaust flow rate from the air-fuel ratio and the fuel rate.

2. The system of claim 1, wherein the controller is further configured to adjust an amount of a reductant inserted into the exhaust gas based on the determined exhaust flow rate.

3. The system of claim 1, wherein the controller is further configured to:
   determine a stoichiometric coefficient comprising a ratio of the air-fuel ratio to a stoichiometric air fuel ratio from the oxygen fraction; and
   determine the air-fuel ratio from the stoichiometric coefficient.

4. The system of claim 1, wherein:
   the oxygen fraction comprises an oxygen molar fraction; and
   the controller is further configured to:
   determine an oxygen mass fraction from the oxygen molar fraction; and
   determine the air-fuel ratio from the oxygen mass fraction.

5. The system of claim 1, wherein the controller is configured to determine the exhaust flow rate using the following equation:
   exhaust flow rate=(1+air−fuel ratio)× fuel rate.

6. The system of claim 1, further comprising:
   a fuel rate sensor configured to be operably coupled to the engine, the fuel rate sensor being configured to determine the fuel rate and generate the fuel rate signal;
   wherein the controller is communicatively coupled to the fuel rate sensor and configured to receive the fuel rate signal therefrom.

7. An aftertreatment system for treating an exhaust gas produced by an engine, the aftertreatment system comprising:
   a selective catalytic reduction system;
   a first sensor comprising a NOx sensor configured to measure an amount of NOx gases in the exhaust gas flowing into the selective catalytic reduction system, the first sensor further configured to measure an amount of oxygen included in the exhaust gas; and
   a controller communicatively coupled to the first sensor, the controller configured to:
   receive a first sensor signal from the first sensor;
   receive a fuel rate signal corresponding to a rate of fuel consumption by the engine;
   determine an oxygen fraction in the exhaust gas from the first sensor signal;
   determine an air-fuel ratio from the oxygen fraction;
   determine a fuel rate from the fuel rate signal; and
   determine an exhaust flow rate from the air-fuel ratio and the fuel rate.

8. The aftertreatment system of claim 7, further comprising a reductant insertion assembly configured to insert a reductant into the selective catalytic reduction system, wherein the controller is communicatively coupled to the reductant insertion assembly and configured to adjust an amount of the reductant inserted into the selective catalytic reduction system based on the determined exhaust flow rate.

9. The aftertreatment system of claim 7, wherein the selective catalytic reduction system comprises:
   an inlet conduit configured to receive the exhaust gas,
   a catalyst formulated to decompose constituents of the exhaust gas, and
   an outlet conduit configured to expel treated exhaust gas,
   wherein the first sensor is positioned in the inlet conduit.

10. The aftertreatment system of claim 7, wherein the controller is further configured to:
    determine a stoichiometric coefficient comprising a ratio of the air-fuel ratio to a stoichiometric air-fuel ratio from the oxygen fraction; and
    determine the air-fuel ratio from the stoichiometric coefficient.

11. The aftertreatment system of claim 7, wherein:
    the oxygen fraction comprises an oxygen molar fraction;
    the controller is further configured to determine an oxygen mass fraction from the oxygen molar fraction; and
    determine the air-fuel ratio from the oxygen mass fraction.

12. The aftertreatment system of claim 7, wherein the controller is configured to determine the exhaust flow rate using the following equation:
exhaust flow rate=(1+air−fuel ratio)× fuel rate.

13. The aftertreatment system of claim 7, further comprising:
a fuel rate sensor configured to be operably coupled to the engine, the fuel rate sensor configured to determine the fuel rate and generate the fuel rate signal,
wherein the controller is communicatively coupled to the fuel rate sensor and configured to receive the fuel rate signal therefrom.

14. A method of determining an exhaust flow rate of an exhaust gas produced by an engine, the method comprising:
determining an oxygen fraction in the exhaust gas;
determining an air-fuel ratio of the exhaust gas based on the oxygen fraction;
determining a fuel rate corresponding to a rate of consumption of a fuel by the engine;
determining the exhaust flow rate from the air-fuel ratio and the fuel rate;
generating an exhaust flow rate signal indicative of the exhaust flow rate; and
adjusting an amount of a reductant inserted into the exhaust gas based on the determined exhaust flow rate.

15. The method of claim 14, further comprising:
determining a stoichiometric coefficient comprising a ratio of the air-fuel ratio to a stoichiometric air-fuel ratio from the oxygen fraction;
wherein the air-fuel ratio is determined from the stoichiometric coefficient.

16. The method of claim 14, wherein:
the oxygen fraction comprises an oxygen molar fraction;
the method further comprises determining an oxygen mass fraction from the oxygen molar fraction; and
the air-fuel ratio is determined from the oxygen mass fraction.

17. The method of claim 14, wherein the exhaust flow rate is determined using the following equation:
exhaust flow rate=(1+air−fuel ratio)× fuel rate.

18. A control circuitry for determining an exhaust flow rate of an exhaust gas produced by an engine, the control circuitry comprising:
a controller configured to be a communicatively coupled to a first sensor, the first sensor configured to measure an amount of NOx gases in the exhaust gas, the controller being configured to:
receive a first sensor signal from the first sensor;
receive a fuel rate signal corresponding to a rate of fuel consumption by the engine;
determine an oxygen fraction in the exhaust gas from the first sensor signal;
determine an air-fuel ratio from the oxygen fraction;
determine a fuel rate from the fuel rate signal;
determine the exhaust flow rate from the air-fuel ratio and the fuel rate; and
generate an exhaust flow rate signal indicative of the exhaust flow rate.

19. The control circuitry of claim 18, wherein the controller is further configured to adjust an amount of a reductant inserted into the exhaust gas based on the determined exhaust flow rate.

20. The control circuitry of claim 18, wherein the controller is further configured to:
determine a stoichiometric coefficient comprising a ratio of the air-fuel ratio to a stoichiometric air fuel ratio from the oxygen fraction; and
determine the air-fuel ratio from the stoichiometric coefficient.

21. The control circuitry of claim 18, wherein:
the oxygen fraction comprises an oxygen molar fraction; and
wherein the controller is further configured to:
determine an oxygen mass fraction from the oxygen molar fraction, and
determine the air-fuel ratio from the oxygen mass fraction.

* * * * *